United States Patent [19]

Uchiyama et al.

[11] Patent Number: 5,047,846
[45] Date of Patent: Sep. 10, 1991

[54] IMAGE PROCESSING EQUIPMENT WITH LIGHT SOURCE SYNCHRONIZED TO BLANKING INTERVAL OF VIDEO CAMERA

[75] Inventors: Shigeru Uchiyama, Hamamatsu; Hideji Fujiwake, Kyoto; Iwayo Nakagawa; Masahiko Hirano, both of Hamamatsu; Yoshinori Mizuguchi, Hamamatsu; Hideshi Oishi, Hamamatsu; Norikazu Sugiyama, Hamamatsu, all of Japan

[73] Assignee: Hamamatsu Photonics K.K., Japan

[21] Appl. No.: 570,249

[22] Filed: Aug. 20, 1990

[30] Foreign Application Priority Data

Aug. 25, 1989 [JP] Japan .................................. 1-219780

[51] Int. Cl.$^5$ ........................ H04N 7/18; H04N 5/335
[52] U.S. Cl. ...................................... 358/93; 358/110
[58] Field of Search .......................... 358/93, 110, 107

[56] References Cited

U.S. PATENT DOCUMENTS

| | | | |
|---|---|---|---|
| 4,675,731 | 6/1987 | Takasu et al. | 358/110 |
| 4,713,686 | 12/1987 | Ozaki et al. | 358/93 |
| 4,878,116 | 10/1989 | Thomas et al. | 358/110 |
| 4,882,498 | 11/1989 | Cochran et al. | 250/571 |

Primary Examiner—John K. Peng
Attorney, Agent, or Firm—Lowe, Price, Leblanc & Becker

[57] ABSTRACT

The present invention relates to an equipment for analyzing the $Ca^{2+}$ concentration in the cardiomyocytes, wherein a fluorescent reagent is loaded into the cells to cause intracellular carboxyl groups to be coupled with $Ca^{2+}$. The cells are subjected to pulse-excited lights of differing in wavelengths during a vertical blanking period following a predetermined period of time after application of the stimulative signal. The signal causes the cells to generate fluorescent images varying in fluorescence intensity due to the difference in the wavelength of the pulse-excited lights. The resultant images generated are captured by a high-sensitivity television camera and displayed on a video monitor. A plural number of image data are obtained by varying the timing of the stimulating signal with the images stored in image memory. Image data is accessed through a central processing unit which two-dimensionally analyzes the change in the shape of a single cardiomyocyte due to the contraction and the dynamic change in the intracellular $Ca^{2+}$ concentration.

3 Claims, 3 Drawing Sheets

IMAGE PROCESSING EQUIPMENT WITH LIGHT SOURCE SYNCHRONIZED TO BLANKING INTERVAL OF VIDEO CAMERA

BACKGROUND OF THE INVENTION

1. Field of the Invention

The present invention relates to an image processing equipment, wherein the sample such as that of the cardiomyocytes is subjected to the stimulus so that the change in the fluorescene with time can be measured at a high time resolution.

2. Description of the Prior Art

In the conventional image pick up method using the television camera, the sample is subjected to an uninterrupted light from the continuously lit light source lamp; the time resolution for obtaining the data cannot be made higher than 1/30 sec, which is the time required for 1 frame, and thus no higher time resolution is not available, so that the data reflecting the change with the time corresponding to the duration of the stimulus cannot be obtained, since the device to give the stimulus to the sample cannot be synchronized with (the television camera); and, for example the change in $Ca^{2+}$ concentration resulting from the contraction of the cardiomyocyte can be measured by the intensity of the fluorescence of the reagent loaded in the cells, but the process (of the change in the $Ca^{2+}$ concentration cannot be observed in details by the conventional method using the television camera, since the contraction of the heart occurs at the rate in the order of milli-second.

There is another method using the photomultiplier tube instead of the television camera, wherein the fluorescence at a point within the visual field of the microscope or the fluorescence of many samples put in the cuvette is measured. This method using the photomultiplier enables as to measure the intensity of the fluorescence at a high time resolution, but the two-dimensional analysis of the fluorescence of the sample is not possible due to the spot detection.

The object of the present invention is to provide an equipment capable of two-dimensionally analyzing the change in the fluorescence at a time resolution such as the milli-second or less order.

Another object of the present invention is to provide an equipment capable of two-dimensionally analyzing the change in the shape of a single cardiomyocyte due to its contraction and the dynamic behavior of the intracellular $Ca^{2+}$ concentration at a time by combining a fluorescence microscope with a television camera.

The objects and other characteristics of the present invention will be described hereunder.

BRIEF SUMMARY OF THE INVENTION

The objects of the present invention are as described above, and the equipment according to the present invention for measuring the change in the sample with the time by a high-sensitivity television camera comprises a pulse-light-up light source to emit the two pulse excitation lights differing in the wavelength during the blanking period of said high-sensitivity television camera, a stimu-lating device for giving the stimulus to the sample at the time preceding to the light emission timing of the pulse-light-up light source by a certain time period and a timing signal generator to generate the timing signals to determine the scan timing of the high-sensitivity television camera, the timing of the pulse excitation light from the pulse-light-up light source and the timing of the stimulating signal from the stimulating device.

In this image processing equipment, a fluorescent reagent is loaded into the sample of the cardiomyocytes to cause the intracellular carboxyl group to be bonded to the $Ca^{2+}$; the external stimulus is given to the cardiomyocyte; the two pulse excitation lights differing in the wavelength are given to said caridomyocyte; and the image of the cardiomyocyte is taken by the high-sensitivity television camera. In this system, the pulse light coincides with the blanking period of the television camera; the stimulus timing is set according to the time of the emission of said pulse excitation light; the television camera is so that image of the sample can be taken by scanning for at least one frame out of the blanking period, whereas the image will not be taken while the sample is exposed to the pulse excitation light. This image processing equipment enables the timing of the stimulus to be varied according to various requirements in measuring, the plural number of image data to be stored in the memory, said image data to be re-synthesized for observing the change in the image and the change in the shape of a single cardiomyocyte occurring at the rate on the milli-second order due to the contraction of the cardio-myocyte and the concurrent dynamic change in the intracellular $Ca^{2+}$ concentration to be analyzed two-dimensionally.

DETAILED DESCRIPTION

An embodiment of the present invention will be explained hereunder in reference to the drawings.

Figure 1:
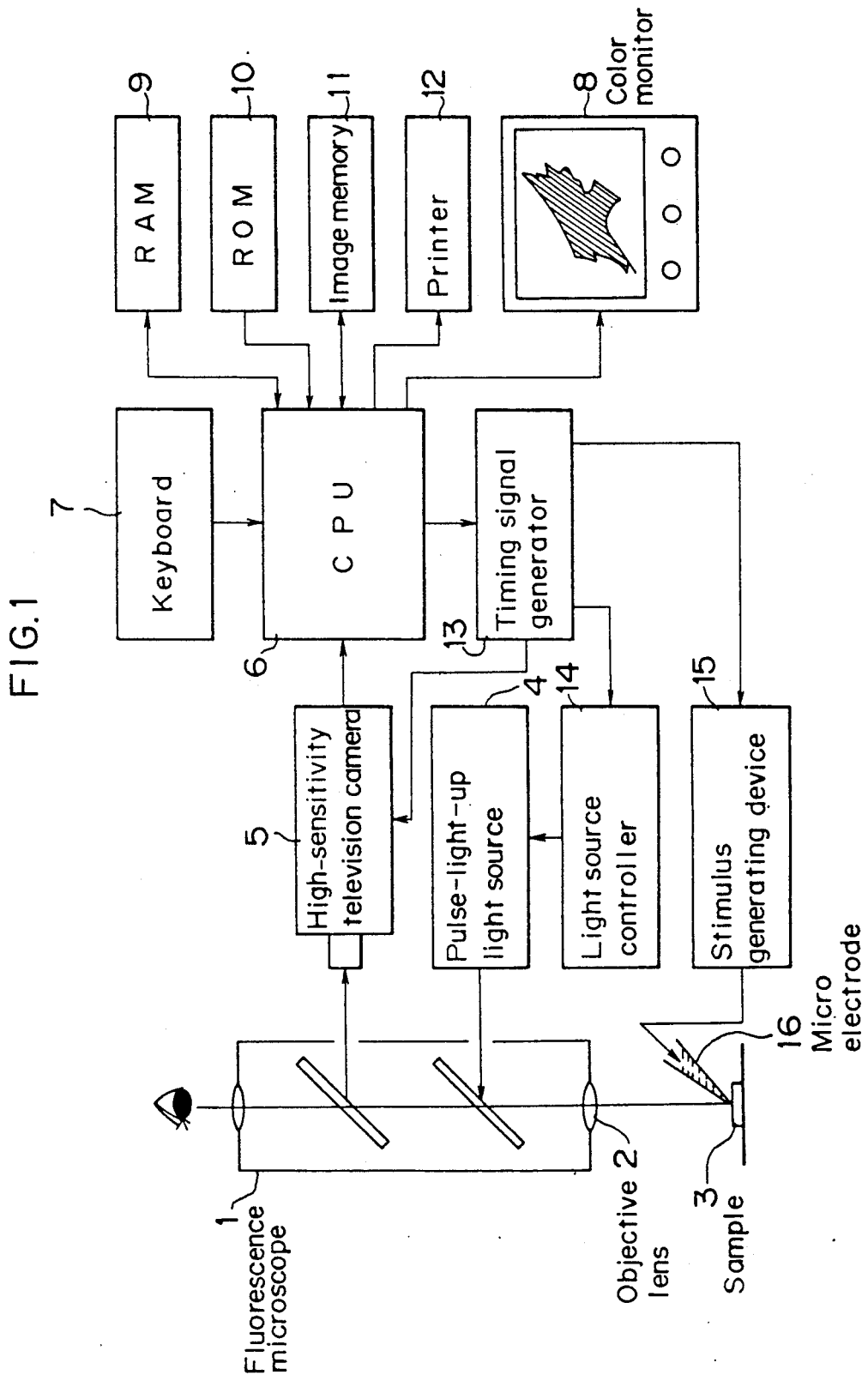
FIG. 1 is a block diagram showing an embodiment of the present invention relating to an image processing equipment.

In FIG. 1, 1 represents the fluorescence microscope, wherein the sample 3 such as that of the cardiomycetes with the fluorescent reagent loaded thereinto is set on the side of the objective lens 2. The pulse-light-up light source 4 to irradiate the sample 3 with the pulse excitation lights of single wavelength or different wavelength. Said high-sensitivity television camera 5 is installed on the output side of said fluorescence microscope 1. The CPU 6 comprising the image processor is connected to the output side of the high-sensitivity television camera. This CPU 6 is connected to the keyboard 7 to input the data for processing, the command for analysis and other data, the color monitor 8 to display the image analysis menu and the data, the RAM 9 for the temporary storage of the image data, the ROM 10 to store the programs for the analysis, processing, reading and storing of the data, the image memory 11 for storing the image data, the printer 12 for printing the measured data and the timing signal generator 13 for generating the timing signal. The timing signal generator 13 generates the drive signal for said sequential-scanning high-sensitivity television camera 5, the timing signal for writing in said image memory 11, the timing signal of the stimulus generator 15 and the pulse-light-up timing signal for the light sourse controller 14.

The operation of the image processing equipment having the above-described composition will be explained next in reference to the drawings.

Figure 2:
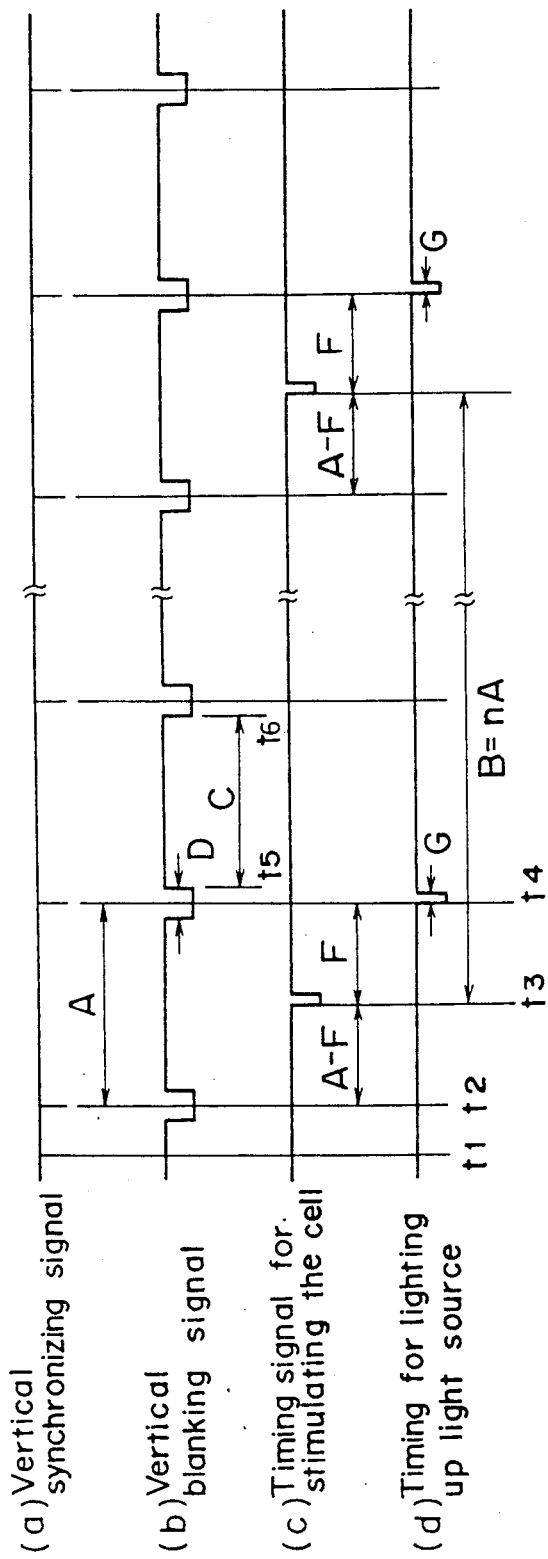
FIG. 2 is a time chart showing the operations of the equipment according to the present invention.
Figure 3:
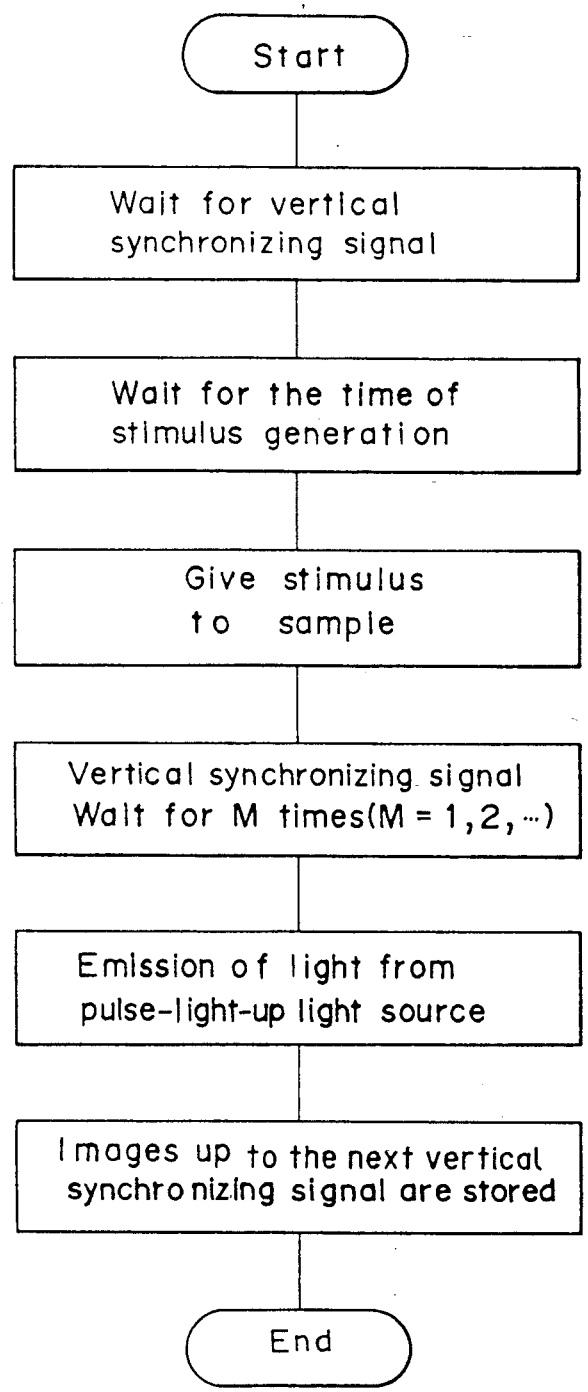
FIG. 3 is a flow chart showing the sequence of the operations of the equipment according to the present invention.

Loading the fluorescent reagent into the sample of the cardiomyocytes 3 causes the intracellular, its carboxyl group to be bonded to the $Ca^{2+}$ in the cardiomyocytes 3. The cardiomyocytes 3 whereinto the fluoroscent reagent is injected is set on the side of the objective lens 2 of the fluorescence microscope 1. The measurement is started at the time $t_1$ shown in FIG. 2. After starting the measurement, wait until the first vertical synchronizing signal is detected, and when the first vertical synchronizing signal is received at the time $t_2$, the timing signal is generated by the timing signal generator 13 at the time $t_3$, which is reached after a predetermined time (A-F) from the time $t_2$, and the generation of this timing signal causes the stimulus signal to be outputted from the stimulus generating device 15. Here, A represents the period of 1 vertical synchronizing signal, while F represents the time from A to any one vertical blanking period. The stimulus signal is outputted at the time of $t_3$, and this causes the micro electrode 16 to apply the stimulating current to cardiomyocytes 3. The timing signal is outputted from the timing signal generator 13 at the time $t_4$, which is in the next vertical blanking period and will be reached after the predetermined time period F from the time $t_3$ for the output of the stimulus signal, and this causes the pulse excitation light from the pulse-light-up light source 4 is projected on the cardiomyocytes 3 through the light source controller 14. Here, it is essential for the pulse excitation light to be in the vertical blanking period D, and this enables the stimulus timing signal to be outputted before the predetermined time when the timing for the output of the pulse excitation light. In the above-described embodiment, the time $t_3$ for outputting the stimulus timing signal is set within 1 frame of the time $t_4$ for the timing of the pulse excitation light, but said output time $t_3$ is not limited within said 1 frame and thus may be set taking more than 1 frame or plural number of frames.

The cardiomyocyte 3 is irradiated with the excitation lights having different wavelength, for example the pulse excitation lights of 340 nm and 360 nm or 340 nm and 380 nm, coming from said pulse-light-up light source 4. This causes the fluorescent images differing in the intensity of the fluorescence depending on the wavelength of the light to depending on the wavelength of the light to be generated from the cardiomyocyte 3, and these fluorescent images are taken by the high-sensitivity television camera 5.

The image signal from said television camera is stored in the image memory 11 through the CPU 6 and displayed on the monitor television 8 or printed by the printer 12. Thus, when the stimulus is given at the time $t_3$, the image can be obtained after a certain period of time F or at the time $t_4$. That is, the stimulus is given at the time $t_3$ preceding to the time $t_4$ for the light-up of the pulse light source, and, after a certain period of time F, the fluorescent image can be obtained during the period C between the time $t_5$ and the time $t_6$ by the scanning with the television camera. The different images can be obtained by varying the time $t_3$ for the timing of said stimulus.

The plural number of image data are stored in the image memory 11, and the stored data are accessed by the CPU for analysis. More particularly, the $Ca^{2+}$ concentration is calculated using the calibration graph of the fluorescence ratio and $Ca^{2+}$. To obtain this calibration graph, the known $Ca^{2+}$ concentrations of some samples are stored in the ROM 10 in advance, and the intensity of the fluorescence of the sample is measured by CPU 6 after processing the sample with the fluorescent reagent and two-different pulse excitation lights.

In the above-described embodiment, the pulse excitation light is generated during the vertical blanking period D of the frame of 1/30 sec., but, where the faster analysis is required, the pulse excitation light may be generated during the horizontal blanking period.

What is claimed is:

1. An image processing equipment for measuring a change in a condition of a sample over time using a high-sensitivity television camera, said image processing equipment comprising:
    a pulse-light-up light source for emitting a pulse excitation light during a blanking period of said high-sensitivity television camera;
    a stimulus generating device for imparting a stimulus to the sample at a time preceding the time at which the light is emitted from said pulse-light-up light source; and
    a timing signal generator for supplying timing signals to said high-sensitivity television camera, pulse-light-up source and stimulus generating device.

2. An image processing equipment according to claim 1, wherein the pulse excitation light from the pulse-light-up light source is emitted during a vertical blanking period of the television camera.

3. An image processing equipment according to claim 1, wherein a plural number of images are obtained by varying the timing of imparting the stimulus to the sample in response to the time of the emission of the pulse excitation light so that a change in the condition of the image can be observed by re-synthesizing a whole image.

* * * * *